United States Patent [19]

Steer

[11] Patent Number: 4,701,169
[45] Date of Patent: Oct. 20, 1987

[54] OSTOMY APPLIANCE WITH IMPROVED ATTACHMENT MEANS

[75] Inventor: Peter L. Steer, Surrey, England

[73] Assignee: Craig Medical Products, Surrey, England

[21] Appl. No.: 902,093

[22] Filed: Aug. 27, 1986

Related U.S. Application Data

[63] Continuation of Ser. No. 681,176, Dec. 13, 1984, abandoned.

[30] Foreign Application Priority Data

| Dec. 19, 1983 | [GB] | United Kingdom | 8333711 |
| Mar. 1, 1984 | [GB] | United Kingdom | 8405415 |
| Apr. 12, 1984 | [GB] | United Kingdom | 8409483 |
| Apr. 19, 1984 | [GB] | United Kingdom | 8410231 |
| May 10, 1984 | [GB] | United Kingdom | 8411906 |
| Jun. 19, 1984 | [GB] | United Kingdom | 8415610 |

[51] Int. Cl.[4] .............................................. A61F 5/44
[52] U.S. Cl. ................................... 604/344; 604/338
[58] Field of Search ............... 604/336, 337, 338, 339, 604/341, 342, 343, 344

[56] References Cited

U.S. PATENT DOCUMENTS

| Re. 29,453 | 10/1977 | Weddle | 604/344 |
| 3,039,464 | 6/1962 | Galindo | 604/344 |
| 3,055,368 | 9/1962 | Baxter . | |
| 3,081,771 | 3/1963 | Lee | 604/344 |
| 3,121,021 | 2/1964 | Copeland . | |
| 3,339,546 | 9/1967 | Chen . | |
| 3,522,807 | 8/1970 | Millenbach | 604/344 |
| 3,604,421 | 9/1971 | Pizzella | 604/344 |
| 3,734,096 | 5/1973 | Millenbach | 604/344 |
| 4,095,599 | 6/1978 | Simonet-Haibe | 604/336 |
| 4,111,205 | 9/1978 | Nemeth | 604/390 |
| 4,192,785 | 3/1980 | Chen et al. . | |
| 4,213,458 | 7/1980 | Nolan et al. | 604/344 |
| 4,393,080 | 7/1983 | Pawelchak et al. . | |
| 4,488,557 | 12/1984 | Engel | 604/336 |

FOREIGN PATENT DOCUMENTS

| 0081907 | 11/1982 | European Pat. Off. . | |
| 2396541 | 3/1979 | France | 604/344 |
| 1256866 | 12/1971 | United Kingdom . | |
| 1568860 | 6/1980 | United Kingdom . | |
| 1571657 | 7/1980 | United Kingdom . | |
| 2119654 | 11/1983 | United Kingdom | 604/344 |

Primary Examiner—C. Fred Rosenbaum
Assistant Examiner—Gene B. Kartchner
Attorney, Agent, or Firm—Lawrence S. Levinson; Robert E. Lee, Jr.

[57] ABSTRACT

An ostomy appliance comprises a body-attachable pad of skin-compatible adhesive material having a stomal orifice, and means whereby a plurality of ostomy bags can be attached in sequence to the pad by exposing a fresh region of adhesive each time it is desired to attach a clean ostomy bag.

12 Claims, 28 Drawing Figures

OSTOMY APPLIANCE WITH IMPROVED ATTACHMENT MEANS

This is a continuation of copending application Ser. No. 681,176, filed on Dec. 13, 1984, now abandoned.

BACKGROUND OF THE INVENTION

This invention relates to an ostomy appliance; pad for same; attachment means for same; and kit of parts for assembling same.

In a successful known system, described and illustrated in British Patent No. 1 571 657, an ostomy bag is attached to a skin-compatible medical grade adhesive pad by a releasable coupling. In the case of some ostomates, however, it may be desirable to provide a lightweight, simple adhesive attachment system.

SUMMARY OF THE INVENTION

According to the present invention, there is provided an ostomy appliance comprising a body-attachable pad of skin-compatible adhesive material having a stomal orifice, and means whereby a plurality of ostomy bags can be attached in sequence to the pad by exposing a fresh region of adhesive each time it is desired to attach a clean ostomy bag.

According to one embodiment of the invention there is provided an ostomy appliance comprising a bag for receiving discharged wastes, a stomal orifice in one wall of the bag, a flange having a flat surface, intended to face towards the body of the wearer when the appliance is worn, surrounding the orifice, a medical grade adhesive pad, and a plurality of double sided adhesive annuli, separated by peelable cover annuli carried by the pad, each of the double sided adhesive annuli having a peripherally projecting portion.

The double-sided adhesive annuli are intended for sequential use in attaching the bag, via its flange, to a pad of medical grade adhesive material which the wearer has attached to his (or her) skin at the peristomal region. The reason for having a plurality of adhesive layers separated by peelable cover annuli is so that a new double sided annulus can be exposed by peeling off the outer cover layer. Hence each time a bag is emptied or changed it can be securely reattached to the medical grade adhesive pad and there is no need to frequently remove the pad. This is a considerable advantage in that the operation of removing and replacing such a pad is one of some difficulty and is often painful.

Such an appliance can be used as a 4-day bag or a 5-day bag by providing a corresponding number of double sided adhesive annuli. Each cover layer may have a radially projecting finger tab which serves two purposes, firstly it can carry a number or indication (e.g. "Monday") and secondly it enables the cover layer to be readily stripped off to expose the adhesive surface of the underlying double sided adhesive layer so that the flat surface of the flange on the bag can be brought into face-to-face contact with the so exposed adhesive surface.

In accordance with one preferred embodiment of the invention, an ostomy bag is attached to a body-attachable pad by a series of sequentially peelable adhesive members each of which has a grasping tab. A flexible microporous layer or tape may be used to assist in attaching the pad to the skin of the wearer. In one embodiment the tabs are arranged so that peeling off a first tab exposes a second tab, the latter not being accessible to the user until the first tab has been peeled off. In another embodiment the tabs are radially extending and angularly spaced apart from tabs of adjacent adhesive numbers.

Alternatively, double sided adhesive layers may be alternated with peelable cover layers, and the cover layers may be shaped and arranged so that they are sequentially peelable, that is to say, each cover layer has a grasping tab and these tabs are so arranged that peeling off one tab exposes an underlying tab. Each cover layer is peeled off when it is desired to expose a fresh region of adhesive in order to attach a clean bag to the pad of skin-compatible material which is adhesively attached to the peristomal region.

In accordance with another preferred embodiment of the invention, there is provided a body-attachable pad carrying a flange to which is adhesively secured a stack of sequentially peelable adhesive members for attaching an ostomy bag to the flange, and the flange and the pad are connected by a flexible web which permits limited relative movement therebetween in a direction substantially perpendicular to the pad. Using such an arrangement, an ostomate can place his/her fingers behind the flange (i.e. between the flange and his body) so as to absorb the pressure which is applied to fix the bag to the exposed one of the stack of plasters.

In accordance with a further alternative embodiment of the invention, a kit of parts for making an ostomy appliance includes an apertured pad of body-attachable, skin-compatible material, and a plurality of ostomy bags to each of which is attached a peelable cover layer which when removed exposes an annular region of adhesive surrounding a stomal orifice in a wall of the bag, the said region of adhesive being arranged in use to adhesively secure each bag in turn to the pad.

In accordance with yet another preferred embodiment of the present invention, the body-attachable, skin-compatible pad is attached to a disc of plastics material (e.g. a vacuum-formable material) having an upstanding rim, there being a closed loop line of weakening within the rim so that a central region of the disc can be manually removed by the user. The aperture so produced serves as a stoma aperture.

In use the user cuts or punctures a hole for his stoma in the pad of skin compatible material and removes the central area of the plastics material; then when the member is applied to the body an inner marginal edge portion of the pad takes up a position closely surrounding the stoma, and forms both a protective pad and a seal. The skin-compatible material then covers the exposed inner edge of the disc and avoids any pain or irritation being caused to the stoma by the inner edge of the disc.

Also according to the invention an adhesive plaster for use in attaching an ostomy bag to a body-attachable member has an adhesive-protecting cover layer which is constructed so that successive separate regions of the cover layer can be torn off in turn, so exposing a fresh adhesive for the attachment of a fresh ostomy bag.

The invention will be better understood from the following non-limiting description of examples thereof given with reference to the accompanying diagrammatic drawings in which:

BRIEF DESCRIPTION OF THE DRAWINGS

FIGS. 15 and 16 illustrate another manner of use of a plaster according to the invention, FIG. 15 being a cross-sectional view taken in a vertical plane and FIG. 16 is a front view of a plaster applied to a body-attachable member.

DETAILED DESCRIPTION OF THE DRAWINGS

In the drawings, like parts bear like reference numerals.

Figure 1:
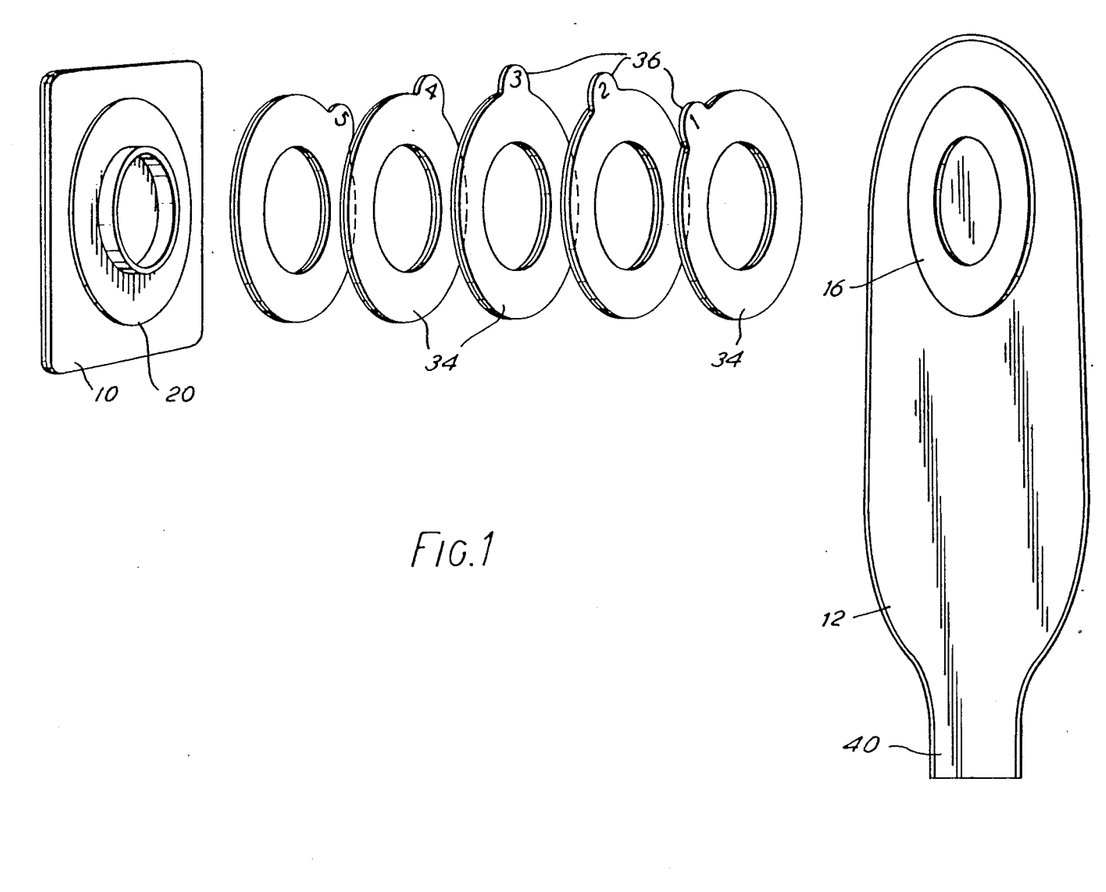
FIG. 1 is an exploded perspective view of a medical grade adhesive pad, a plurality of double sided adhesive annuli, and intervening cover annuli.
Figure 2:
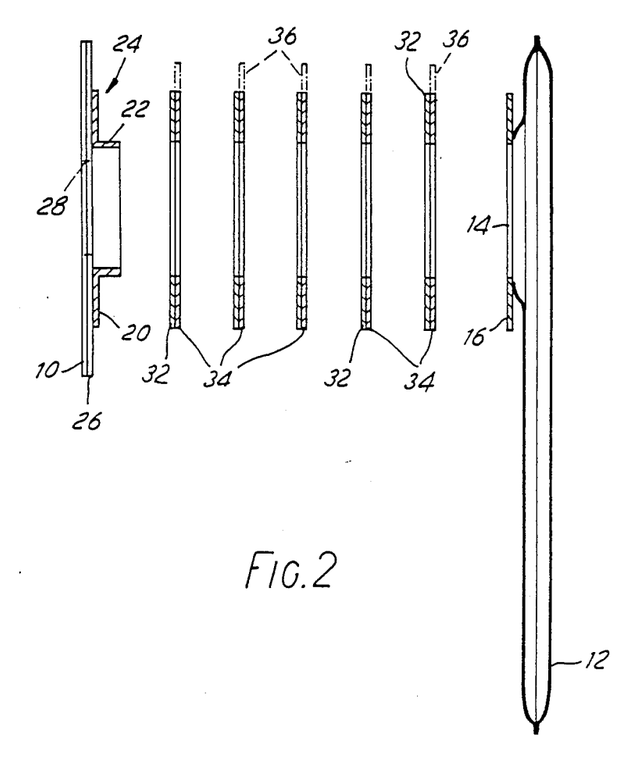
FIG. 2 is a side view corresponding to FIG. 1.

Referring firstly to FIGS. 1 and 2, the illustrated ostomy appliance includes a medical grade adhesive pad 10 and an ostomy bag 12. The ostomy bag has a stomal orifice 14 which is surrounded by a flange, e.g. of synthetic plastics material, having an annular flat surface which is intended to face towards the body of the wearer when the appliance is in use. This surface is indicated at 16. The medical grade adhesive pad 10 also has secured thereto a flange 20 which optionally includes an inner peripheral rib 22. The flange 20 has an outwardly facing flat annular surface 24, intended to receive a stack of double sided adhesive annuli which are interleaved with annular cover layers. The medical grade adhesive pad 10 may be bonded to a plastics film layer 26, in conventional manner. In use, a hole indicated by the dotted lines 28 is cut in the pad 10 and the film 26 so that the user's stoma can be passed therethrough.

Suitable medical grade adhesives comprise pressure sensitive adhesive formulations that consist of a homogeneous blend of one or more water soluble or water swellable hydrocolloids dispersed in a viscous elastomeric substance such as polyisobutylene as disclosed by Chen in U.S. Pat. No. 3,339,506. Optionally, the adhesive composition can also include one or more cohesive strengthening agents described by Chen et al. in U.S. Pat. No. 4,192,785 or one or more hydratable natural or synthetic polymers as described by Pawelchak et al. in U.S. Pat. No. 4,393,080. Other medical grade adhesives designed for ostomates and available on the market are also suitable.

The double-sided adhesive annuli are indicated at 32, and for example, five are here shown. This would be appropriate for a 5-day ostomy appliance. The fifth one in order of use is directly adhesively attached by one of its adhesive surfaces to the surface 24 and by its other surface to a peelable annular cover layer 34. Like cover layers are located between adjacent double sided adhesive annuli, and these cover layers as seen best in FIG. 1 each have a radially projecting finger tab 36 useful firstly for peeling off the layer 34 and secondly for carrying a numeral or other visible indication to assist the user of the appliance.

The bag 12 may be either a bag having a drain outlet 40 as seen in FIG. 1, or may alternatively be a closed bag intended to be thrown away when full, as seen in FIG. 2.

The words "annulus" and "annuli" are used in the application without a strict geometrical meaning. That is to say, a double sided annulus as used in this invention need not be geometrically circular; a double sided adhesive layer of any shape which surrounds the stomal orifice and which can be peeled off from an adjacent layer to expose a region of adhesive would be suitable.

Figure 3:
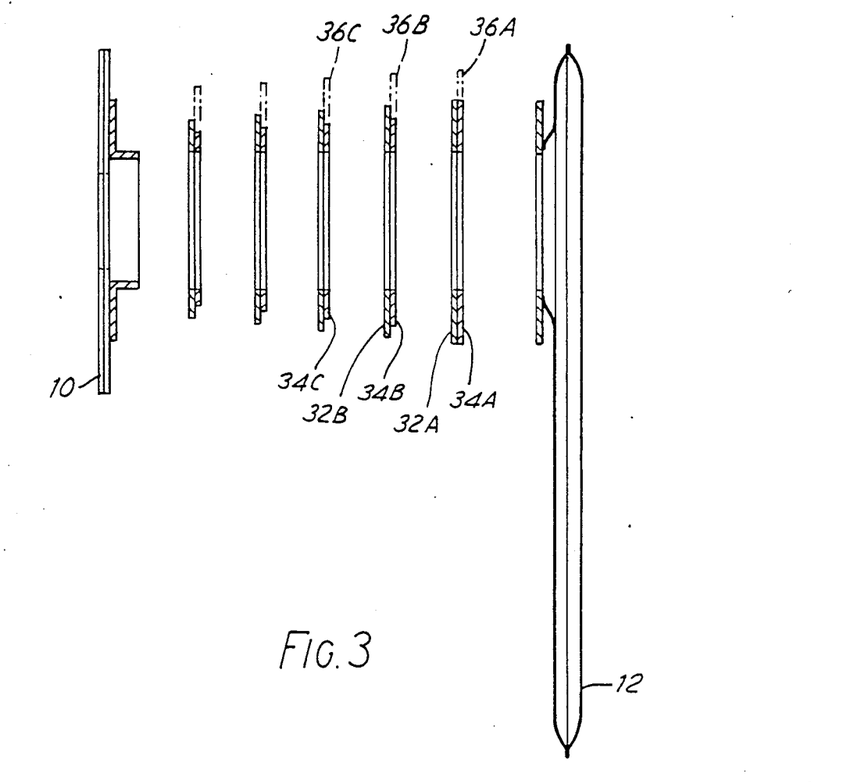
FIG. 3 is a side view of an alternative embodiment of the invention.

Referring now to FIG. 3, the ostomy bag 12 and medical grade adhesive pad 10 are as shown previously. The double sided adhesive annuli interleaved with peelable cover annuli however have a gradually diminishing outside diameter as one moves from the first to be used (nearest to the bag) to the last to be used (nearest to the pad). The reason for this is to ensure that when one peelable cover layer (e.g. 34A) is removed, it exposes an area of fresh adhesive on the double sided adhesive annulus 32A, and then when the next cover layer 34B is removed, a fresh layer of adhesive on the annulus 32B is exposed. Deterioration of the outer edges of the adhesive annuli is thereby minimized.

Another feature of difference compared to the FIGS. 1 and 2 embodiment is that the O.D. of the adhesive layers is greater than that of the cover layers (except for the peel tabs thereof). Consequently narrow outer rims of the adjacent adhesive annuli tend to stick together and prevent any peel apart occurring except at the surface where the outermost peel-off cover annulus is being removed.

Figure 4:
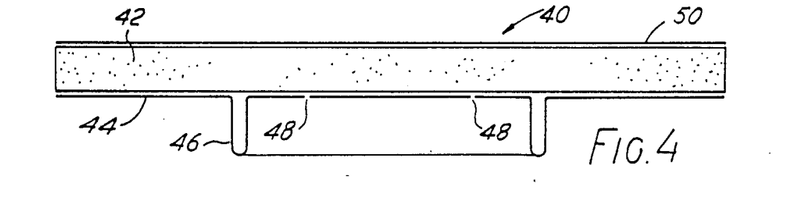
FIG. 4 is a cross-sectional diagrammatic view, somewhat enlarged from full size, of an example of a body attachable member according to the invention.
Figure 5:
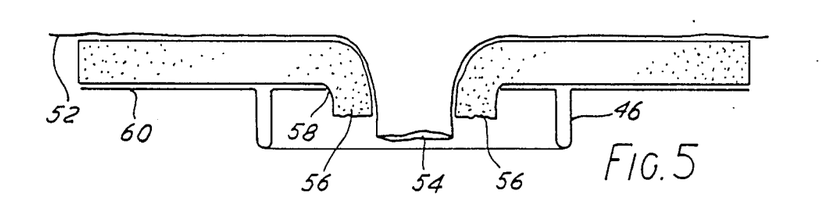
FIG. 5 is a view similar to FIG. 4 showing the member in position on a wearer and illustrating the cushioning and sealing effect of a marginal portion of the pad.

Referring now to FIGS. 4 and 5, a body-attachable member or pad 40 comprises a pad 42 of medical grade skin compatible adhesive fixed to a disc 44 of plastics material. The disc 44 has an upstanding rim 46, and a closed loop line of weakening, which may be circular, indicated at 48 to define an area within the rim 46 which can readily be removed by a user without the use of a tool.

A strippable protective layer 50 is applied to the rear surface of the pad 52. This layer 50 is stripped off to expose an adhesive surface of the pad 52 when the pad 40 is to be applied to the patient's body.

FIG. 5 illustrates the member 40 in position, the skin of the patient being indicated at 52 and the stoma of the patient at 54. As will be seen, the inner marginal edge portion 56 of the pad 42 has been deformed somewhat so that it closely surrounds and is in contact with the periphery of the patient's stoma 54; this provides a cushioning effect preventing the relatively sharp inner rim 58 of the disc 44 from painfully digging into the patient's stoma, and moreover the good adhesive contact between the pad 42 and the stoma 54 provides a sealing effect preventing any migration of liquid waste products towards the peristomal skin area 52. The annular surface 60 of the disc 14 serves for adhesive attachment of an ostomy bag in any of the various ways described in this patent application.

In a preferred form of the present invention, the rim 46 is produced by vacuum forming.

By use of the manufacturing procedure disclosed in FIG. 3, of our British Patent Application No. 84 10231 a large number of body attachable members can be readily produced without the need for individual molding of plastics disks having rim parts.

Figure 6:
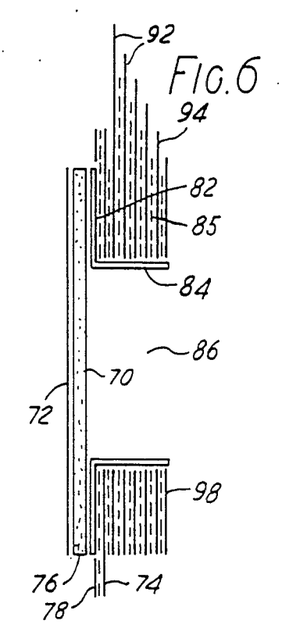
FIGS. 6 and 7 show, in cross-section and in front elevation respectively, one embodiment of a skin-compatible medical grade adhesive pad carrying a plurality of "peel off" adhesive annuli.
Figure 7:
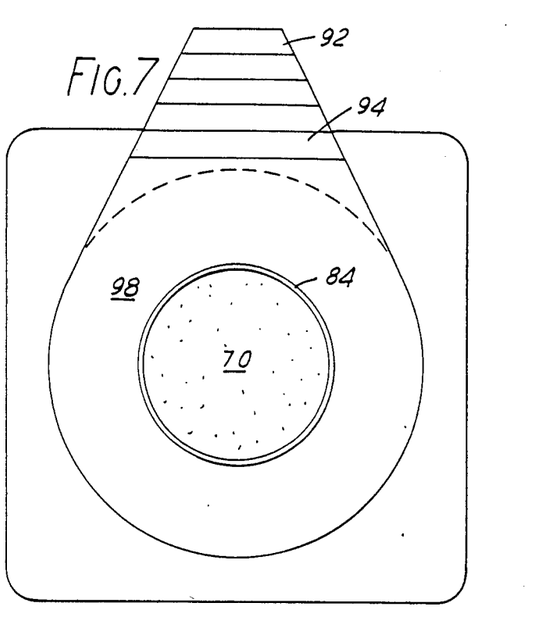

An alternative embodiment of the present invention is illustrated in FIGS. 6 and 7. As seen in FIGS. 6 and 7, a pad 70 of skin-compatible medical grade adhesive material such as that described above, and carrying a strippable rear cover layer 72 supports a front cover sheet 74 whose function is to cover over the edges 76 of the pad 70 which would otherwise be exposed, there being a strippable annular paper or like layer 78 which protects adhesive on the rear surface (left hand side as seen in FIG. 6) of the protective layer 74 where this extends beyond the pad 70. As illustrated, the pad 70 is in the form of a flat disc and the protective layer 74 is substantially rectangular. Attached to the pad 70 is a plastics disc 82 carrying a central circular rim 84 which defines a stomal aperture 86. The disc 82 carries, stacked over the layer 74, a stacked pile of annular adhesive attachment members, herein called plasters, each plaster being constituted by a layer of tough paper or flexible plastics film bearing adhesive 85 and having a grippable tab 92. The tab arrangement as illustrated in FIG. 6 is such that the rearmost plaster has the largest tab and the forwardmost plaster has a relatively small tab as seen at 94. The assembly is protected by a front cover annular layer of release paper or other suitable material which is identified at 98.

It will be seen that by peeling off firstly the cover layer, an annular region of adhesive is exposed to which an ostomy bag may be applied, and after that bag has been filled, then by peeling off the first adhesive plaster 94 further fresh adhesive on the so-exposed face of the next underlying plaster is made available for attaching a subsequent ostomy bag to the appliance.

Figure 8:
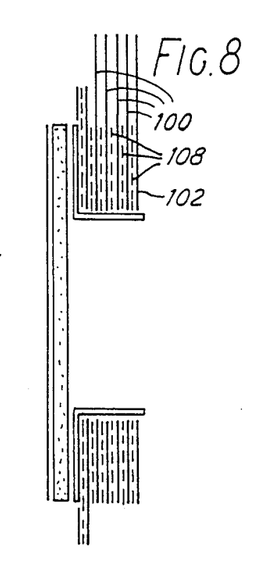
FIGS. 8 and 9 show, in cross-section and in front elevation respectively, a second embodiment of a pad carrying a different arrangement of "peel off" adhesive annuli.
Figure 9:
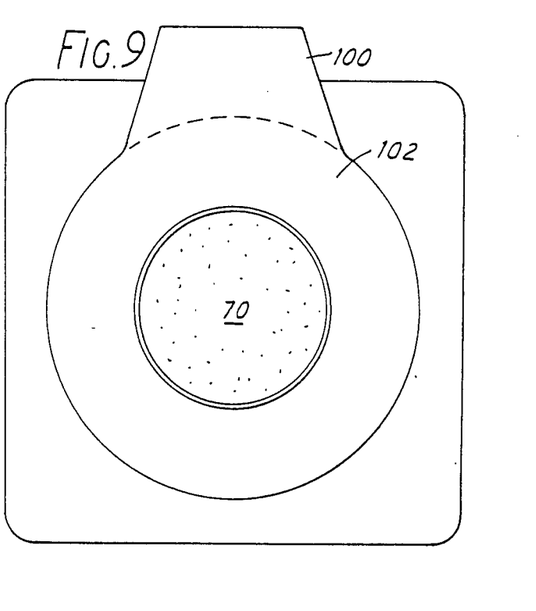

FIGS. 8 and 9 show an alternative version of this embodiment of the invention, the difference being that in this embodiment the tabs of the adhesive plasters 100 are all of the same size. As seen in FIGS. 8 and 9, no adhesive is provided between the plasters outside the annular region, so that one tab can readily be separated from the next and so that the cover sheet 102 can be removed at the beginning of the use of the appliance.

Figure 10:
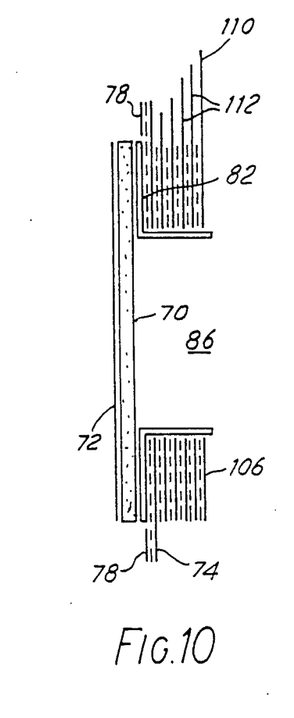
FIGS. 10 and 11 show, in cross-section and in front elevation respectively, a third embodiment of pad carrying yet another arrangement of "peel off" adhesive annuli.
Figure 11:
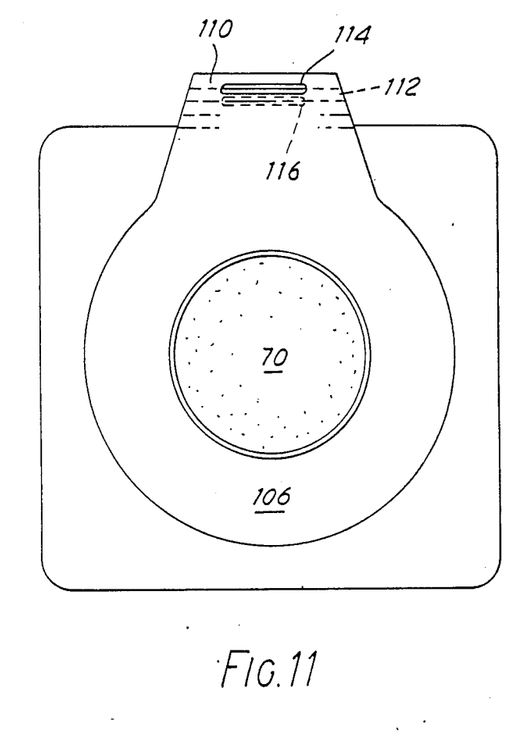

Another variation of this embodiment of the invention is illustrated in FIGS. 10 and 11. According to this advantageous version, each of the cover layers 106 and the plasters 108 is annular in form with an upwardly projecting tab, the tab being denoted 110 in the case of the cover layer and 112 for each of the plasters. Each of the plasters has a tab of progressively increasing height, moving from the plaster closest to the disc 82 to the plaster furthest from the disc 82. Moreover, each tab has an elongated slot cut therein, near to the top of the tab, to enable a user to insert his fingernail in the slots so as to more readily separate one tab from the next. The slot in the cover layer is indicated at 114 and the aperture in the front tab 112 is indicated at 116. For simplicity of illustration in FIG. 11, the other apertures in the tabs 108 are not shown.

Referring to the versions of the invention shown in FIGS. 6-11, it will be realized that any convenient numbers of separate plasters may be employed. Although five plasters have been illustrated in FIG. 6, and four plasters in FIGS. 8 and 10, any selected number of plasters, e.g. one for each day of the week, can be included in the appliance. Moreover, while in some instances it may be preferable for the ostomy bag which is to be used with the illustrated appliances to have a relatively stiff plastics flange surrounding the stomal orifice in one of its walls, in other instances no such stiff flange would be needed and the bag wall could be adhesively secured directly to the exposed adhesive surface.

Figure 12:
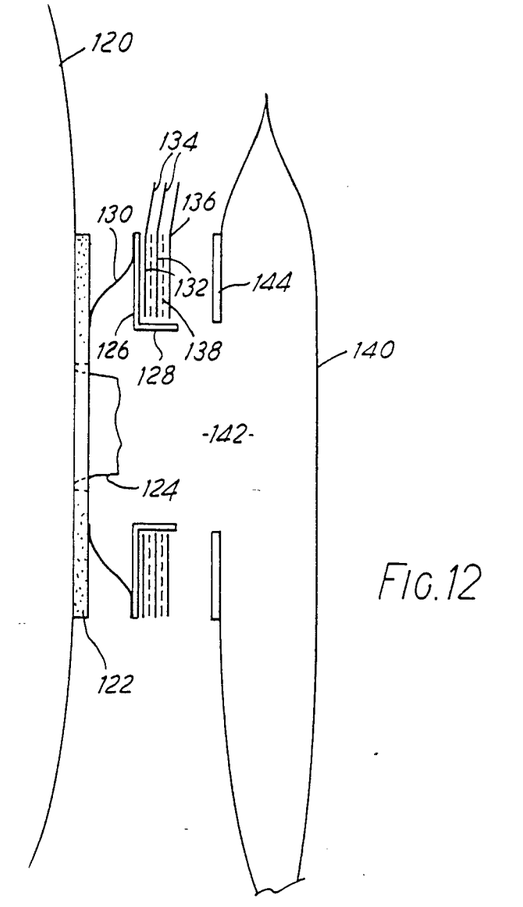
FIG. 12 diagrammatically shows a further embodiment of a body-attachable pad together with an ostomy bag.

An alternative embodiment of the invention is shown in FIG. 12, which is a diagrammatic cross-section illustrating the skin 120 of a wearer with a body-attachable pad 122 of medical grade adhesive material such as that referred to above. The stoma of the patient is seen at 124, projecting through a suitable hole in the pad 122. A disc 126 carrying a circular rim 128 is connected to the pad 122 by a flexible annular sheet 130. The sheet 130 may be of fabric or of a thin flexible plastics film.

The disc 126 carries a stack of annular plasters 132, each of which has a tab 134. A strippable protective front cover layer 136 protects the adhesive 138 on the outermost plaster. An ostomy bag 140 having a stomal aperture 142 surrounded by a flat thin plate of annular form 144 cooperates with the body-attachable appliance including the pad 122. In use, the protective layer 136 is stripped off exposing the adhesive layer 138 and the bag is brought in face to face manner up against this adhesive, the rim 128 then extending just within the confines of the stomal orifice 142. The bag is consequently held firmly in position on the disc 126 and during the assembly, the user can if he wishes place his fingers behind the disc 126 to support the disc 126 against the pressure needed to press the plate 144 onto the adhesive 138. When the bag 140 is full, it is removed, the used plaster is also removed so exposing a fresh adhesive surface on the plaster beneath. A new bag can then be applied in a similar way.

The illustrated adhesive plaster 210 (FIGS. 13 and 14) includes a substrate 212 (which may for example be a conventional fabric substrate as found in conventional sticking plasters) having a central hole 214 therein to constitute a stomal aperture. The rear (body side) surface of the substrate carries adhesive 216 whereby the plaster can be fixed to a body-attachable member 218, not shown in FIG. 14. The front (or bag side) surface carries adhesive 220 which is covered by a peelable protective layer 222. The layer 222 is divided into five annular regions 222a to 222e by circular partial cuts 224 which extend through, for example, about ¾ of the thickness of the protective layer 222. These cuts may be made by a punching or stamping operation. Alternatively the cuts may extend completely through the layer 222, or lines of weakening may be produced by having rows of perforations. Other expedients will occur to a man of average skill in the art.

Figure 13:
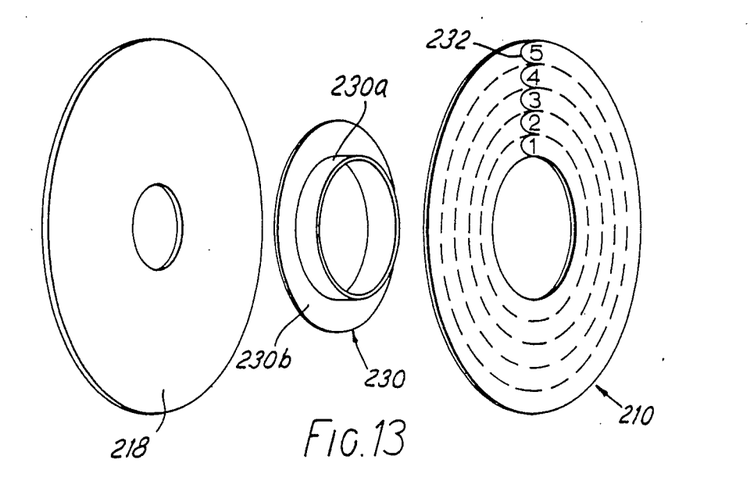
FIG. 13 is an exploded view illustrating another embodiment of the invention.
Figure 14:
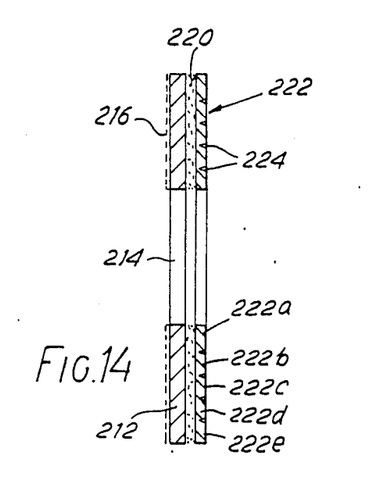
FIG. 14 is a cross-section taken in a vertical plane through the adhesive plaster shown in FIG. 13 with the thickness exaggerated for clarity of illustration.

While a circular hole 214 and circular cuts 224 have been described, it will be appreciated that a non-circular, e.g. oval, configuration could be employed although circular is preferred.

In use of the assembled appliance, an intervening member 230 herein called a chute member is fixed to a body-attachable pad 218 of medical grade adhesive and the cylindrical wall 230a of the chute is passed through the hole 214, the latter being of a sufficient size to accommodate the chute. The chute functions to guide any waste products issuing from the stoma into the interior of an ostomy bag and to minimize the chance of any of them coming into contact with the adhesive 216 or the adhesive 220. If such contact were to occur, the security of attachment provided by the adhesive would be made less reliable. However, in some instances, e.g. when a very simple and inexpensive ostomy system is desired, the chute 230 can be omitted and the plaster 10 attached directly by the adhesive 216 to the pad 218.

In use, the inner ring 222a is peeled or stripped off, so exposing an annular area of adhesive 220, and the wall of an ostomy bag having a stomal orifice therein is brought in face to face contact with the exposed area of adhesive 220, with the stomal orifice in the bag wall substantially in registry with the hole 214. To facilitate stripping off the rings 222a to 222e, each ring may carry a tab or projection 32 which can be grasped between finger and thumb. The tabs may if desired by numbered as shown in FIG. 13.

The ostomy bag employed may be of the kind which has a flat annular flange on its rear wall surrounding the stomal orifice therein, or such a flange may be omitted and the bag rear wall directly applied to the adhesive 220.

The intermediate member 230 may advantageously be made by vacuum forming a synthetic plastics film, and its flange 230b is preferably ultrasonically welded to a plastics film forming the outer surface boundary of the pad 218.

In an advantageous embodiment of the invention, the adhesive 216 may be such as to have a higher "peel strength" than the adhesive 220. This ensures that the attachment of the plaster 210 to the pad 18 remains secure when force is applied to peel off one of the rings 222a to 222e.

Figures 15, 16:
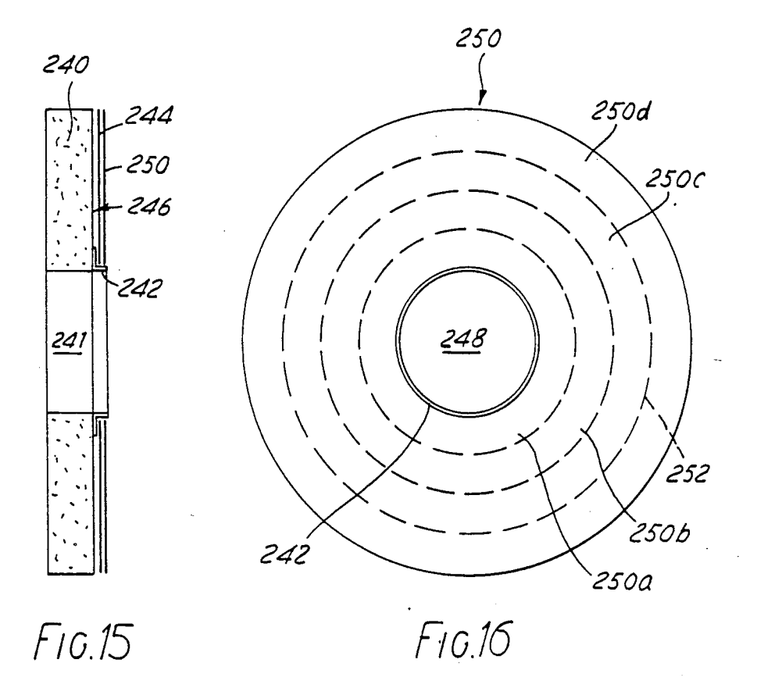

FIG. 15 illustrates a body-attachable medical grade skin-adherable pad 240 which is disc-shaped with a central hole 241, i.e. is annular in shape. To the pad 240 is attached a vacuum formed plastics rim 242. An adhesive plaster 244 according to the invention is directly fixed in any suitable way, e.g. by adhesive, to the front face 246 of the pad 240. The plaster 240, 242 has a central hole 248 of a diameter slightly greater than the O.D. of the rim 242. A protective layer 250 can be manually peeled or stripped from the plaster 244. The layer 250 is separated by cuts 252 into concentric rings 250a to 250d (FIG. 15). Each of these rings can be separately stripped from the plaster 244. While the plaster 244 and pad 240 are shown as circular in shape, they could have other configurations.

The pad 218 or the pad 240 may be made of a medical grade adhesive as described above.

An advantageous form of body-attachable pad consists of three layers, namely a skin compatible medical grade adhesive, a plastics film thereon, and a Fasson fabric plaster layer covering the film and having its marginal edge portions extending somewhat beyond the outer edges of the adhesive and the film. The adhesive and the film will normally be coextensive. The purpose of the Fasson fabric layer is to shield the edges of the adhesive so that, for example, these edges do not slide to the clothing of the wearer.

Figures 17, 18:
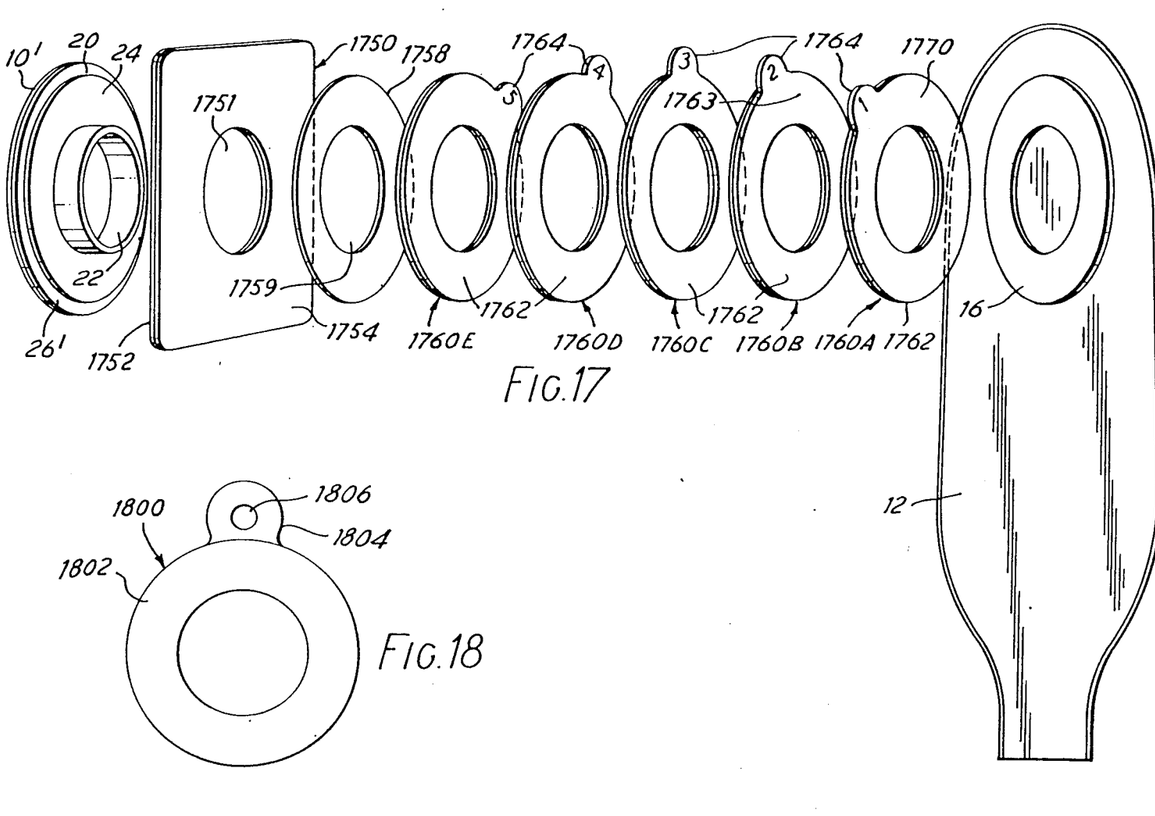
FIG. 17 is an exploded perspective view of a medical grade adhesive pad, a porous adhesive layer, and a plurality of peelable adhesive members with angularly offset projecting tabs.
FIG. 18 is a front elevational view of one of the peelable adhesive members of FIG. 17.

Referring now to FIG. 17, an alternative embodiment of the present invention ostomy appliance of FIGS. 1 and 2 is shown in exploded view. The ostomy appliance includes a flexible microporous tape designated generally 1750 having an aperture 1751 therethrough to accommodate rib 22. The diameter of the aperture 1751 is larger than the diameter of rib 22 but smaller than the diameter of flange 20. Tape 1750 comprises adhesive layer 1752 that overlaps flange 20 and any of plastics film 26' not affixed to flange 20. Outer surface 1754 of the microporous tape is a porous backing layer.

In FIG. 17, tape 1750 is larger in area than pad 10' and square or rectangular in shape. In use adhesive surface 1752 is pressed onto the body a distance from the stoma and aids the adhesive pad 10' in maintaining the ostomy appliance in place. Medical adhesive pad 10' and plastics film layer 26' are the same as pad 10 and layer 26 of FIG. 1 except they are circular in shape and generally smaller in area.

The term microporous is used in connection with adhesive layer 1752 because layer 1752 appears to be continuous but when viewed under a microscope it is sponge-like having randomly located channels and voids. The layer 31 can be of the acrylic type as taught by Copeland in U.S. Pat. No. 3,121,021, or it can be made of the same ingredients as pad 10 with the microporosity resulting from a difference in processing. See European Patent Application No. A1 0081 907. This microporous tape can also be employed as adhesive layer 74 in the embodiment shown in FIGS. 6 to 11.

Porous backing layer 1754 can be formed of woven or non-woven fabric such as the rayon web described by Copeland in U.S. Pat. No. 3,121,021, an open mesh polymeric substance such as an open mesh polyethylene or polypropylene or a polymeric foam such as polyurethane foam, polyethylene foam, etc., or a non-woven material made from polyester fibers, polypropylene fibers, nylon fibers, composite olefin fibers, or cellulose fibers which are commercially available.

The tape 1750 while aiding in attaching the ostomy appliance to the user is flexible and allows the skin to breathe resulting in a more comfortable attachment.

Tape 1750 is affixed to the flange surface 24 not only by its own adhesive layer 1752 but also by an overlapping member 1758 such as a plastics film having an adhesive layer on each side. Member 1758 has an aperture 1759 therethrough which is slightly larger then the diameter of rib 22. The outer diameter of member 1758 is larger than the aperture 1751 in tape 1750. Member 1758 overlaps both a portion of flange 20 adjacent rib 22 and a portion of side 1754 of tape 1750.

In FIG. 17, the peelable adhesive members are indicated at 1760, and for example, five are shown, 1760A to 1760E. Each member comprises a layer of tough paper or flexible plastics film bearing an adhesive layer 1762 and having a grippable tab 1764. The tab arrangement is such that each is angularly displaced from the tab of an adjacent member around the common axis of the members 1760. The fifth peelable adhesive member 1760E, the last in order of use (i.e. the one nearest the member 1758), is directly adhesively attached to the outwardly facing adhesive surface of member 1758. It will be remembered that member 1758 comprises a double adhesive layer, one on each side thereof. The non-adhesive surfaces of each of the remaining members (those surfaces which face pad 10') are attached to the adhesive surface 1762 of the previous member which faces the surface 16 of bag 12.

The outermost peelable member 1760A, the first one to be used, has attached thereto a suitable protection cover layer 1770 which protects the outer adhesive layer 1762 of the first member 1760A until use.

FIG. 18 is a front elevational view of a member 1800 suitable for use as member 1760 in FIG. 17 but showing in more detail an alternative embodiment of tab 1762. The member 1800 preferably is made of a clear flexible plastics film with one surface such as the outward facing surface 1802 coated with an adhesive. The member 1800 further comprises a circularly shaped grippable tab portion 1804 having an opening 1806 therethrough. The tab is large enough to be easily gripped by the wearer's fingers and the opening 1806 assists therein.

Figure 19:
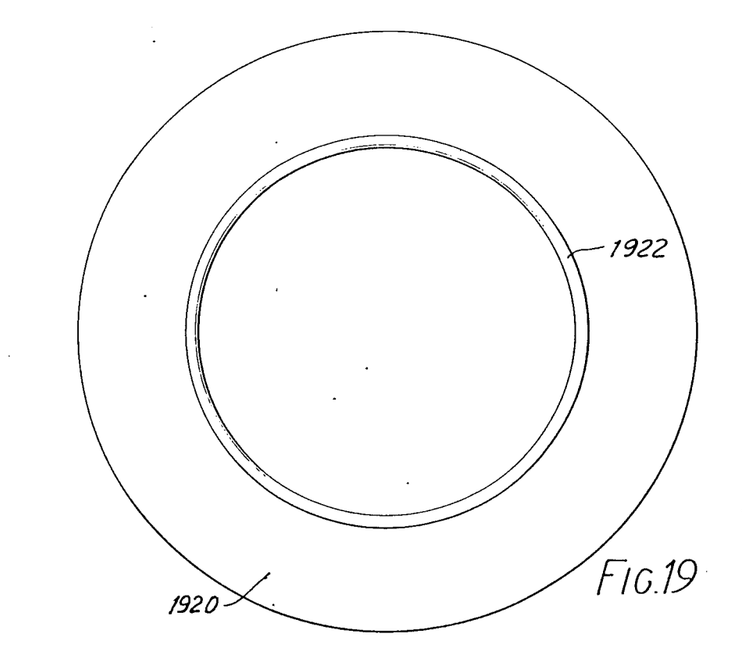
FIGS. 19, 20 and 21 illustrate a tapered or angled rib feature of one embodiment of the present invention, FIG. 19 being a front view, FIG. 20 a vertical axial cross-section, and FIG. 21 being an enlargement of part of FIG. 20.
Figures 20, 21:
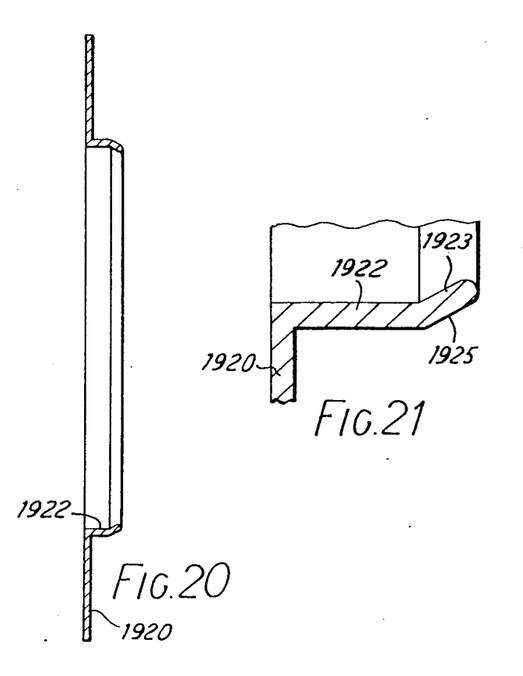

FIGS. 19-21 illustrate an alternative design of a flange member for attachment to the medical grade adhesive pad 10 illustrated in FIG. 1. This flange member 1920, like the flange member 20 of FIG. 1, has an inner peripheral rib 1922. In order to provide a "lead-in" when a user is attaching a bag to an exposed adhesive surface of one of the peelable adhesive members, the inner end, that is to say the end of the rib which extends towards the ostomy bag when the ostomy bag is being applied and which extends into the ostomy bag when it is secured, it canted inwardly as seen best in FIG. 21 at 1923. Consequently, a tapered annular outer surface 1925 is provided which assists a wearer of a bag in bringing the stomal orifice of the bag properly into registry with the flange member 1920.

Figure 22:
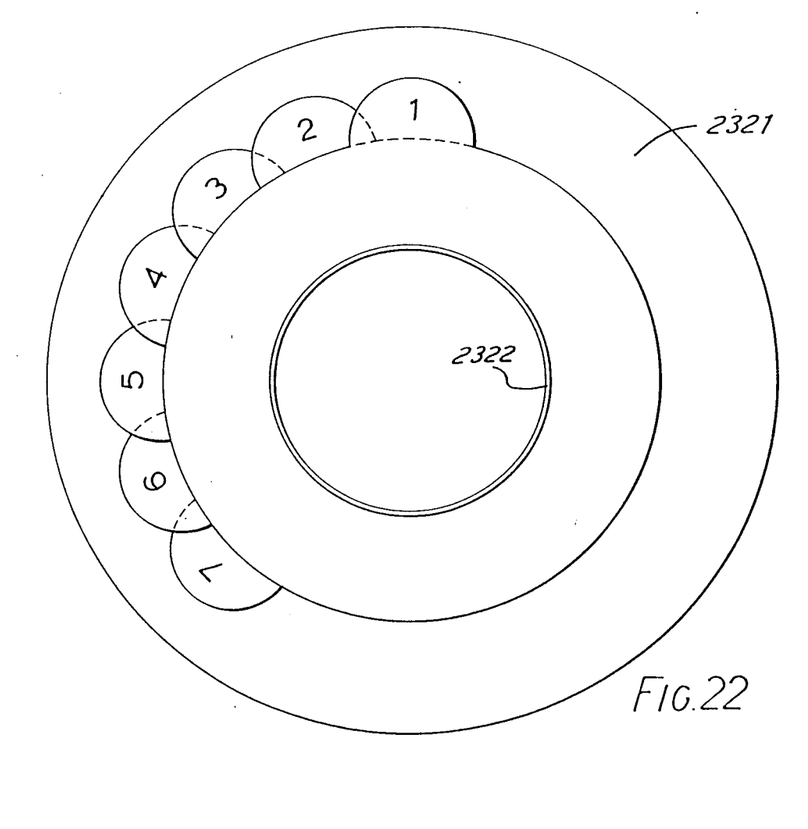
FIGS. 22 and 23 are front view and vertical axial cross-sections of an embodiment of the invention wherein a marginal portion of the bag wall surrounding the stomal aperture acts as a wiper to wipe the peripheral rib of the body-attachable flange.
Figure 23:
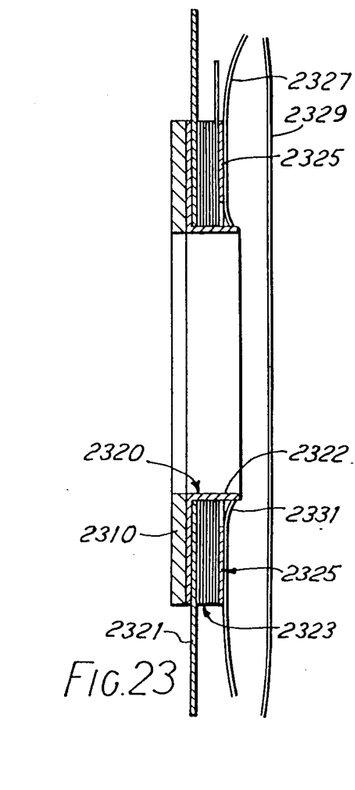

In another embodiment of the invention, there are provided seven peelable adhesive members which may for example be numbered 1-7, and may be arranged in the manner illustrated in FIG. 22. Referring to FIGS. 22 and 23, a medical adhesive pad is shown at 2310, the flange thereon at 2320, and a layer of self adhesive fabric 2321 is placed over the flange 2320 beneath the base of the stack of peelable adhesive members 2323.

A flat annular plastics washer 2325 is secured to a wall 2327 of an ostomy bag whose other wall is seen at 2329. The flat annular washer 2325 may be of plastics material and is constructed so that it has a central circular orifice whose diameter is somewhat greater than the outside diameter of the substantially cylindrical rib wall 2322. The material of the bag wall 2327 however extends inwardly of the inner edge of the washer 2325, and in use acts to wipe against the outside wall of the rib 2322 so tending to keep this outside wall clean of waste materials. It will be appreciated that because the diameter of the stomal orifice in the washer 2325 is greater than the outside diameter of the rib wall 2322, applying the bag to the flange does not require a careful and "fiddy" adjustment of relative positions.

Figures 24, 25:
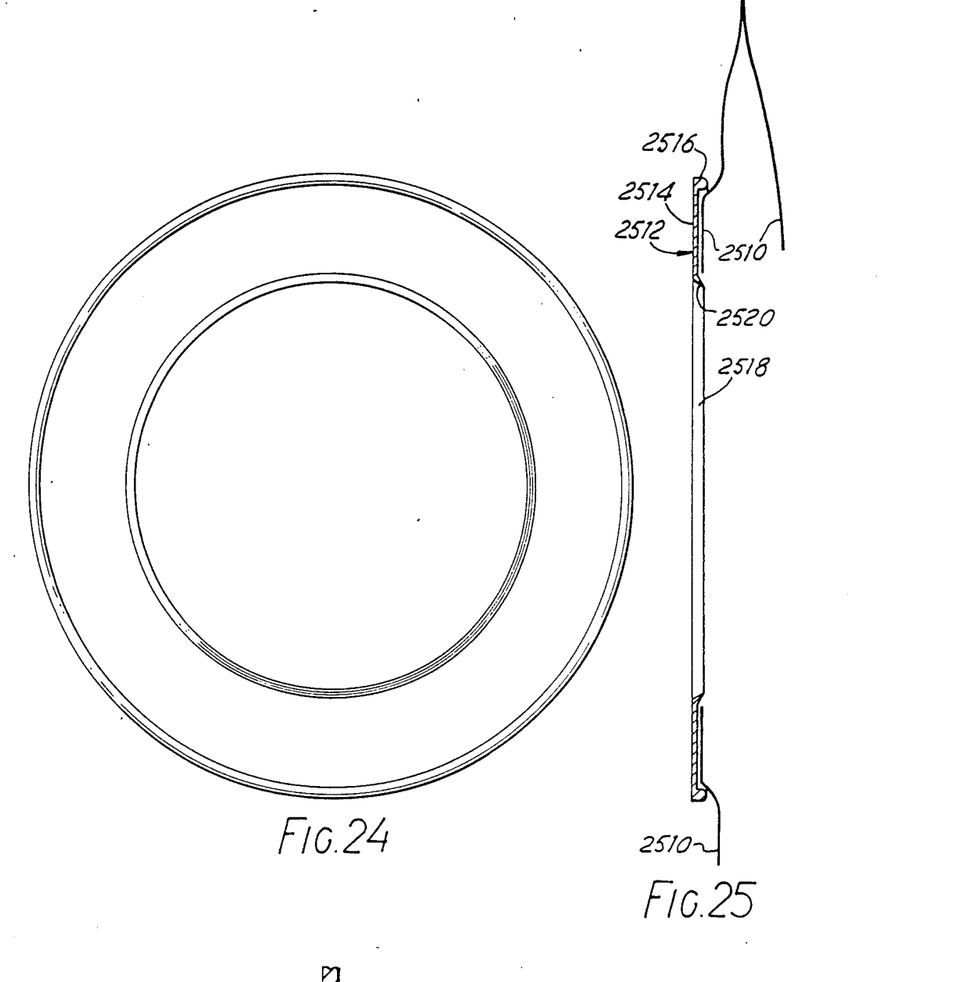
FIGS. 24 and 25 are like views respectively of a washer or flange for attachment to an ostomy bag to render it highly suitable for use as a peel-off bag.
Figure 26:
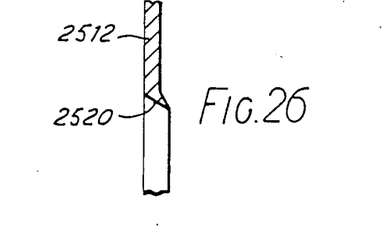
FIG. 26 is an enlargement for clarity of part of FIG. 25.

Instead of utilizing a plain, flat annular washer such as 2325 shown in FIG. 23, one may instead employ a washer for attachment to an ostomy bag of the form shown in FIGS. 24 and 25. This washer may for example be of ethylene vinyl acetate polymer and, referring to FIGS. 24-26, is attached to an ostomy bag surrounding the stomal aperture thereof, the bag being show at 2510. The washer 2512 has one annular flat surface 2514 intended for presentation to the exposed adhesive of one of the peelable adhesive members. There is a beading 2516 at the outer rim of the washer 2512. The inner margin of the stomal aperture 2518 in the washer 2512 is formed by a flexible deflectable seal strip 2520 forming part of the washer 2512. This seal strip 2520 serves a similar function to the inner portion 2331 of the bag wall 2327 (FIG. 23) in that it assists in wiping waste material clear of the cylindrical rib portion of a flange such as flange 2320. Equally, it would act similarly in relation to the external cylindrical surface of the rib 1922 illustrated in FIG. 20.

Figure 27:
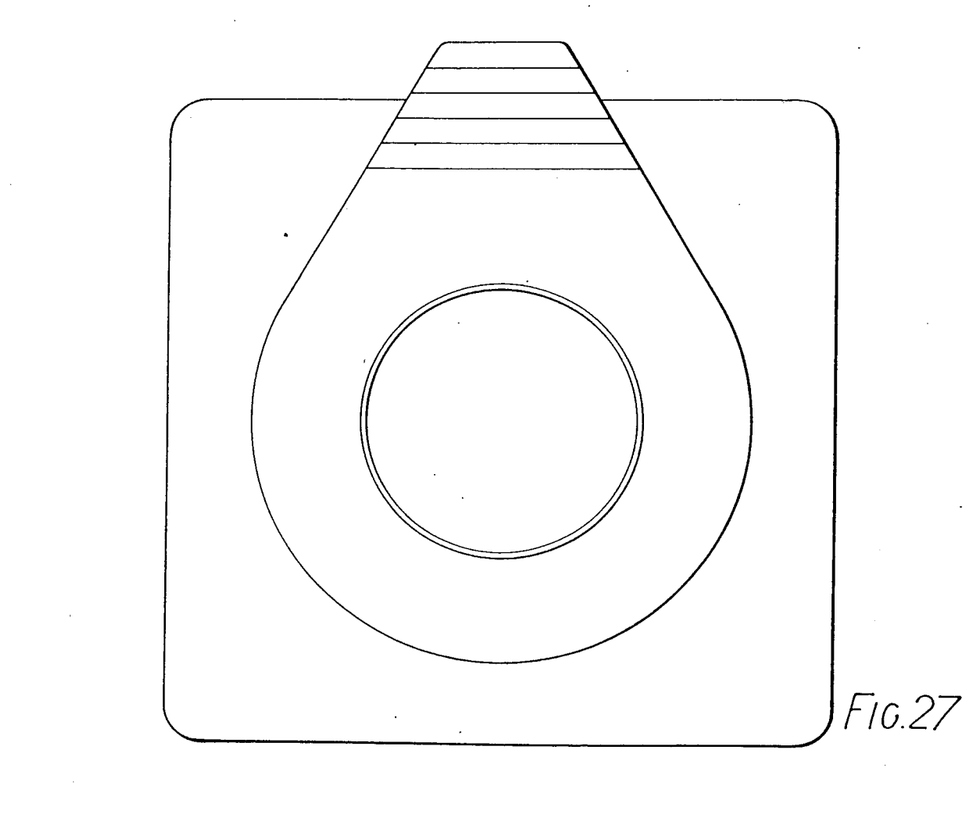
FIGS. 27 and 28 are a front view and a vertical axial cross-section, respectively, of an ostomy appliance and bag illustrating a stack of peelable adhesive members and a tapered rim on a peripheral rib of the body side flange.
Figure 28:
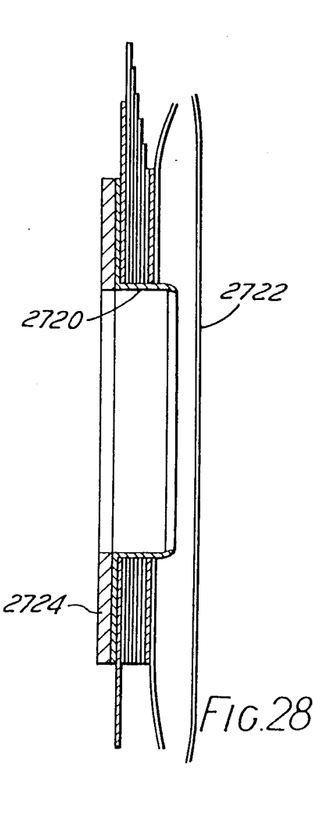

FIGS. 27 and 28 illustrate a flange 2720 which is substantially in accordance with the design illustrated in FIGS. 19-21 assembled in conjuction with an ostomy bag 2722 and a medical grade adhesive pad 2724. The bag 2722 is of course not shown in FIG. 27, and the arrangement of peelable adhesive members is similar in broad concept to that illustrated in FIG. 6 of the present patent application.

While there have been suggestions in the past, e.g. in British Patent Specification No. 1 256 866, that an ostomy bag can be attached to a body-attachable ring by adhesive, there has been (to the best of Applicants' knowledge and belief) no means hitherto suggested or obtainable other than recent patent applications of the present Applicant whereby a series of ostomy bags can be adhesively attached in turn to a single body-attachable member, while the member remains attached to the body of the wearer.

Moreover, the arrangement according to the invention is light in weight, has a very flat configuration, does not produce an unsightly bulge under the clothes, and is easily and inexpensively manufactured.

I claim:

1. An ostomy appliance comprising a bag for receiving discharged wastes, a stomal orifice in one wall of the bag to receive a stoma of a patient, a flange having a flat surface, intended to face towards the body of the wearer when the appliance is worn, surrounding the orifice, a medical grade adhesive pad, and a stack of double sided adhesive annuli, one on top of the other, for attaching the flange of the bag to the pad, said stack of annuli interleaved with peelable cover annuli, said stack and cover annuli carried by the pad and adapted to encircle the patient's stoma, each of the double sided adhesive annuli having a peripherally projecting portion.

2. The appliance of claim 1 wherein said double sided adhesive annuli have a gradually diminishing outside diameter with the annuli closest to the pad having the smallest diameter and the annuli farthest from the pad, the largest.

3. The appliance of claim 2 wherein the outside diameter of each of said annuli is greater than that of the associated cover layer.

4. An ostomy appliance comprising a bag for receiving discharged wastes, a stomal orifice in one wall of the bag to receive a stoma of a patient, a medical grade adhesive pad, and a stack of peelable annular member, one on top of the other and carried by said pad for attaching the bag to the pad and adapted to encircle the patient's stoma, each having a layer of adhesive on one side thereof and a peripherally projecting portion.

5. The appliance of claim 4 wherein the peripherally projecting portions of adjacent members are angularly spaced apart from one another.

6. The ostomy appliance of claim 4 wherein the peripherally projecting portion comprises an opening therethrough.

7. The ostomy appliance of claim 4 wherein said appliance further comprises a microporous tape attached to said medical grade adhesive pad for aiding in the attachment of said appliance to the body of the wearer.

8. A body-attachable pad carrying a flange to which is adhesively secured a stack of sequentially peelable adhesive annular members, one on top of the other, for attaching an ostomy bag having a stomal orifice to receive a stoma of a patient to the flange, said annular members adapted to encircle the patient's stoma, and the flange and the pad are connected by a flexible web which permits limited relative movement therebetween in a direction substantially perpendicular to the pad, whereby an ostomate can place his/her fingers behind the flange, between the flange and his body, so as to absorb the pressure which is applied to fix the bag to the exposed one of the stack of adhesive annular members.

9. An ostomy appliance comprising a bag for receiving discharged wastes, a stomal orifice in one wall of the bag for receiving a stoma of a patient, a washer attached to the wall of the bag and having a flat surface intended to face towards the body of the wearer when the appliance is worn and an inner edge surrounding the periphery of said stomal orifice, a medical grade adhesive pad carrying a flange having an inner peripheral rib which encircles the stoma of the patient, and adhesive means for adhesively attaching said bag to said flange, said bag wall extending inwardly of the inner edge of said washer surrounding said stomal orifice to contact the the rib on its surface opposite the stoma, said adhesive means comprising a plurality of peelable annular members having an adhesive layer on at least one side thereof and carried by said pad, said annular members adapted to surround the patient's stoma.

10. The appliance of claim 9 wherein said a plurality of peelable annular members comprises at least seven members.

11. The appliance of claim 9 wherein said appliance further comprises: a layer of self adhesive fabric placed between said flange and said plurality of peelable annular members.

12. The appliance of claim 4 wherein said peripherally projecting portions are arranged so that peeling off a first peripheral portion exposes a second pheripheral portion, the latter not being accessible to the user until the first peripheral portion has been peeled off.

* * * * *